United States Patent
Bronshtein et al.

(10) Patent No.: US 6,872,357 B1
(45) Date of Patent: Mar. 29, 2005

(54) FORMULATION OF PRESERVATION MIXTURES CONTAINING SENSITIVE BIOLOGICALS TO BE STABILIZED FOR AMBIENT TEMPERATURE STORAGE BY DRYING

(75) Inventors: Victor Bronshtein, San Diego, CA (US); Lynn Linkowski, San Diego, CA (US)

(73) Assignee: Quadrant Drug Delivery Limited, Ruddington (GB)

( * ) Notice: Subject to any disclaimer, the term of this patent is extended or adjusted under 35 U.S.C. 154(b) by 508 days.

(21) Appl. No.: 09/721,609

(22) Filed: Nov. 22, 2000

(51) Int. Cl.⁷ .......................... B01J 19/00; A61L 11/00; A01N 1/02
(52) U.S. Cl. .............................. 422/41; 422/1; 435/1.3; 435/243
(58) Field of Search .................. 435/1.3, 243; 422/41, 422/1

(56) References Cited

U.S. PATENT DOCUMENTS

| | | | |
|---|---|---|---|
| 5,290,765 A | | 3/1994 | Wettlaufer et al. |
| 5,766,520 A | * | 6/1998 | Bronshtein .................. 264/4.6 |
| 6,306,345 B1 | * | 10/2001 | Bronshtein et al. ........... 422/41 |
| 6,509,146 B1 | * | 1/2003 | Bronshtein .................. 435/1.3 |
| 6,537,666 B1 | * | 3/2003 | Bronshtein ............... 428/402.2 |

FOREIGN PATENT DOCUMENTS

| | | |
|---|---|---|
| DE | 1792196 | 5/1972 |
| GB | 799644 | 8/1958 |
| WO | WO 91/18091 | 11/1991 |
| WO | WO 99/27071 | 6/1999 |
| WO | WO 00/40696 | 7/2000 |

* cited by examiner

Primary Examiner—Krisanne Jastrzab
(74) Attorney, Agent, or Firm—Leon R. Yankwich; Michael R. Wesolowski; Yankwich & Associates, P.C.

(57) ABSTRACT

This invention relates to formulations and methods for preserving sensitive biologicals, viruses, bacteria and eukaryotic cells by drying. More particularly, the invention relates to preservation mixtures containing viruses or cells and protectants, including a combination of a methylated monosaccharide and a disaccharide, or oligosaccharide, wherein the mixtures are adapted to stabilize these during dehydration and subsequent storage at ambient and higher temperature.

18 Claims, 5 Drawing Sheets

FORMULATION OF PRESERVATION MIXTURES CONTAINING SENSITIVE BIOLOGICALS TO BE STABILIZED FOR AMBIENT TEMPERATURE STORAGE BY DRYING

BACKGROUND OF THE INVENTION

1. Field of the Invention

This invention relates to formulations and methods for preserving sensitive biologicals, viruses, bacteria and eukaryotic cells by drying. More particularly, the invention relates to preservation mixtures comprising viruses or cells and protectants, wherein the mixtures are adapted to stabilize these samples during dehydration and subsequent storage at ambient and higher temperatures.

2. Description of the Related Art

Sensitive biomolecules, viruses, bacteria, vectors, eukaryotic cells, and small multicellular specimens have a broad range of uses, including for example, human and veterinary pharmaceuticals, immunizations and vaccines, molecular biology, gene therapy, as well as in the food industries. Typically, these bioactive materials, viruses and cells are active in aqueous environments; thus, conventional formulations of such samples have been in aqueous solutions. However, many bioactive materials, particularly viruses and cells, are sensitive to degradation and loss of activity and/or viability in aqueous solutions, particularly at ambient or higher temperatures. Accordingly, such samples often require refrigeration or have short shelf lives under ambient conditions.

Bioactive materials, viruses and cells can be destroyed via a number of chemical mechanisms known in the art. Water is a reactant in nearly all of these destructive pathways. Further, water acts as a plasticizer, which allows unfolding and aggregation of proteins. Since water is a participant in almost all degradation pathways, reduction of the aqueous solution or suspension of bioactive materials, viruses and cells to a dry powder provides an alternative formulation methodology to enhance the stability of such samples. Viruses and cells can be dried using various techniques, including freeze-drying, foam-dying, spray-drying and dessication. Aqueous solutions of biomolecules, viruses and cells are dried and stored as dry powders until their use is required.

In addition to dehydration, vitrification represents another significant approach to preservation (stabilization) of sensitive biomolecules, viruses, and cells. Vitrification can be achieved in the dry state at ambient temperatures, as well as in an aqueous environment under cryogenic conditions (freezing). Ambient temperature stability in the dry state is extremely desirable for many reasons, including storage convenience and economics, transportation, flexibility of delivery options, applicability to emergency situations and access to third world countries. Consequently, vitrification of biomolecules, viruses and cells in the dry state is particularly desirable. However, drying of unprotected biomolecules, viruses and cells, like freezing of such samples, may be very damaging. Therefore, there is a need to develop preservation mixtures in which biomolecules, viruses and cells can be dehydrated and vitrified with minimum loss of their activity or viability.

SUMMARY OF THE INVENTION

The present invention relates to a preservation mixture comprising a biological which is sensitive to loss of activity or viability during drying and storage at ambient or higher temperatures, a non-reducing derivative of a monosaccharide, and at least one additional protectant selected from the group consisting of non-reducing disaccharides, non-reducing oligosaccharides, non-reducing derivatives of disaccharides, non-reducing derivatives of oligosaccharides, proteins, polymeric protectants, and monosodium salt of glutamic acid (MSG).

In a preferred aspect, the biological in the preservation mixture is selected from the group consisting of sensitive biological molecules, viruses, bacteria, other prokaryotic cells, and eukaryotic cells.

The preservation mixture has a total solute mass. In one mode, the modified non-reducing derivative of a monosaccharide comprises between about 5% and 80% wt % of the total solute mass. More preferably, the modified non-reducing derivative of a monosaccharide comprises between about 20% and 60% wt % of the total solute mass.

The preservation mixture in accordance with one preferred mode of the present invention is a methylated monosaccharide. More particularly, the methylated monosaccharide is methyl α-glucopyranoside or methyl β-glucopyranoside.

Where the preservation mixture includes a non-reducing disaccharide, it may be sucrose or trehalose. The protein included in the preservation mixture may be selected from the group consisting of gelatin, albumin, whey albumin or globulin, and a stress protein. In one mode, the protein may be any protein which is stable in aqueous medium at a temperature of greater than about 50° C., and at a pH of greater than about 9 or less than about 5. Preferably, the protein concentration is greater than about 3 wt % and more preferably, greater than about 10 wt. %. The polymeric protectant used in accordance with one mode of the present invention may be selected from the group consisting of HES, PVP, cyclodextrin and PEG.

Where MSG, non-reducing disaccharides, and/or non-reducing oligosaccharides are included in the preservation mixture, these additional protectants may comprise between about 5% and 80% wt % of the total solute mass, and more preferably, between about 20% and 60% wt % of the total solute mass. Where oligosaccharides are employed in the preservation mixture, they are preferably not raffinose, in accordance with one embodiment of the invention.

The preservation mixture is preferably formulated so that it will not crystallize during drying and subsequent storage for at least two weeks. Preferred formulations include: the ratio of sucrose to methyl (α or β) glucose is between about 4:1 to about 1:2; and the ratio of sucrose to MSG is between about 10:1 to about 1:4.

The present invention is also related to a method of preserving a biological which is sensitive to loss of activity or viability during drying and storage at ambient or higher temperatures. The method comprises mixing the biological with a protectant comprising a modified non-reducing derivative of a monosaccharide and at least one additional compound selected from the group consisting of non-reducing disaccharides, non-reducing oligosaccharides, non-reducing derivatives of disaccharides, non-reducing derivatives of oligosaccharides, proteins, polymeric protectants, and monosodium salt of glutamic acid (MSG) to form a preservation mixture (as detailed above), and drying the preservation mixture, wherein at least a portion of the activity or viability of the biological is retained during the drying process and during subsequent storage at ambient or higher storage temperatures. This method is well suited for preservation of viruses, bacteria, other prokaryotic cells, and eukaryotic cells.

The method disclosed is applicable to a variety of drying protocols including, freeze-drying, desiccation, spray-drying, fluidized bed drying, drying in a vacuum, drying in a dry atmosphere, and drying by foam formation.

In a variation to the disclosed method, mixing further comprises at least two steps including loading the virus or cell with the non-reducing derivative of a monosaccharide and then adding the at least one additional compounds to form the preservation mixture. Loading may be achieved by equilibration of the biological in a solution containing the non-reducing derivative of a monosaccharide.

DETAILED DESCRIPTION OF THE PREFERRED EMBODIMENT

A. Definitions

Figure 1A:
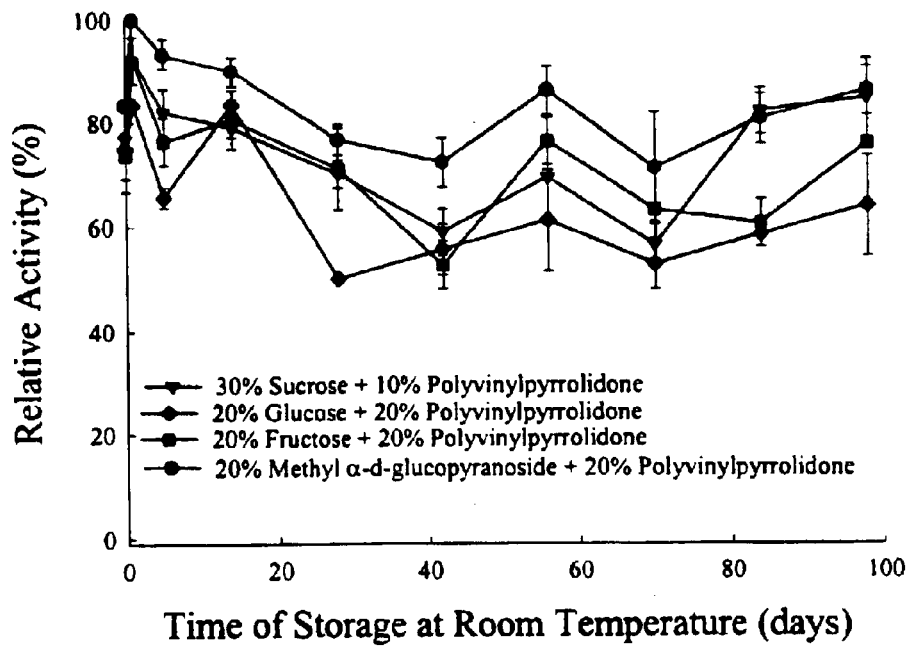
FIG. 1A shows the effect of reducing and non-reducing sugars on ICDH activity during storage at room temperature.

As used herein, the term "chemical stability" and/or "preservation" means that degradation of the biological material by chemical pathways such as oxidation, hydrolysis or enzymatic action, for example, does not exceed an acceptable level. In other words, at least a level of biological activity or viability sufficient for the intended commercial application of the material is retained. In a preferred mode of the invention, a formulation is considered preserved if at least 20% of the biological activity or viability is retained upon rehydration after storage for one week at 37° C.

The term "sensitive biologicals" encompasses peptides, polypeptides, proteins, enzymes and coenzymes, serums, vitamins, antibodies, and antibody fragments. Both naturally-derived or purified and recombinantly produced moieties are included in these terms. This term also includes lipoproteins and post-translationally modified forms, e.g., glycosylated proteins. Analogs, derivatives, agonists, antagonists and pharmaceutically acceptable salts of any of these are included in these terms. The term also includes modified, derivatized or non-naturally occurring peptides having D- or L-configuration amino acids.

In a preferred mode of the present invention, the biologicals include any antigenic substance, capable of inducing an immune response. More particularly, the antigen may be a protein or fragment thereof expressed on the extracellular domain of a tumor (e.g., for the treatment of cancer), an allergen, or a infectious agent of portion thereof (e.g., virus or bacteria). The term "vaccine" refers to a particular type of immunization, where the bioactive material is an infectious agent (or any part thereof), which is administered to a mammal to establish resistance to the infectious disease caused by the agent. Vaccines may include viruses, bacteria and parasites, viral particles and/or any portion of a virus or infectious disease agent or pathogen, including proteins and/or nucleic acids, which may be immunogenic and therefore useful in the formulation of vaccines.

In another aspect, the present invention also encompasses viral, bacterial and yeast-derived vectors useful in transformation of cells. Such vectors may be used for gene therapy as well as molecular biology and genetic engineering. In a most preferred aspect, the term "sensitive biologicals" also includes any virus, prokaryotic and eukaryotic cells, as well as certain small multicellular specimens.

The phrase "preservation by foam formation" refers to a scaleable procedure for drying sensitive biologics by boiling under vacuum under conditions wherein the biologics retain activity or viability for extended periods of time at ambient and higher temperatures. The specific methodological limitations encompassed by the phrase "preservation by foam formation" are detailed below, in two parts, (1) Primary Foam-Drying and (2) Stability Drying/Vitrification, and are disclosed in U.S. Pat. No. 5,766,520 to Bronshtein.

The term "modified non-reducing monosaccharides" are used in accordance with the present invention to refer to a general class of sugars. The modifications may be any known chemical modifications, methylated, ethylated and chlorinated derivatives being preferred. The methyl derivatives include both the α and β forms of the monosaccharides. Consequently, the term "methyl (α or β) glucose" is used. In several the examples, one particular modified non-reducing monosaccharides, methyl α-d-glucopyranoside is used; this compound has been abbreviated MAG.

B. Preservation of Biological Materials

Dehydration of biological specimens at elevated temperatures may be very damaging, particularly for example, when the temperatures employed for drying are higher than the applicable protein denaturation temperature. To protect the samples from the damage associated with elevated temperatures, the dehydration process may be performed in steps or by simultaneous increase in temperature and extent of dehydration. Primary dehydration should be performed at temperatures that are sufficiently low to permit dehydration without loss of biological activity. The preservation methods employed in accordance with the present invention are disclosed in U.S. Pat. No. 5,766,520 to Bronshtein and co-pending U.S. patent application Ser. Nos. 08/979,458 and 09/306,137, 09/589,381, 09/194,499 and 09/254,563, and co-pending U.S. Provisional Application Nos. 60/149,795, 60/166,928 and 60/161,204; the disclosures of which are herein incorporated in their entirety by reference thereto.

In a preferred mode of the present invention, retention of biological activity or viability may be maximized during dehydration of viruses or cells by selecting drying parameters based on the following criteria: (1) protection of dehydrated internal and external molecules, envelopes, membranes and other biological structures is optimized by loading the viruses or cells with protective chemicals, (2) loading may be achieved by equilibration of the viruses or cells in loading solutions containing permeating protectants, (3) the glass transition temperature of the protectant-loaded viruses or cells is preferably raised above the desired ambient storage and/or delivery temperatures, and (4) the mixture of viruses or cells and protectant formulations preferably remains at least partially in an amorphous state during drying and subsequent storage.

Protectant Formulations—A variety of polyols and polymers are known in the art and may serve as protectants as long as they enhance the ability of the biologically active material to withstand drying and storage and do not interfere with the particular biological activity. Indeed, the protectant molecules provide other advantages during preservation (see infra, as an aid to generating mechanically stable foams) besides stabilizing biological materials during dehydration. More particularly, the protectants in accordance with the present invention may include, without limitation, simple sugars, such as sucrose, glucose, maltose, sucrose, xylulose, ribose, mannose, fructose, raffinose, and trehalose, non-reducing derivatives of monosaccharides and other carbohydrate derivatives, sugar alcohols like sorbitol, synthetic polymers, such as polyethylene glycol, hydroxyethyl starch, polyvinyl pyrrolidone, polyacrylamide, and polyethyleneamine, and sugar copolymers, like FICOLL and Dextran, and combinations thereof. Low molecular weight, highly soluble proteins may also serve as protectants.

In one preferred variation of the present invention, where cells, viruses, viral particles and/or viral and non-viral vectors are being preserved, the protective composition may further comprise mixtures of a low molecular weight sugar, a disaccharide, oligosaccharide and polymer including biological polymer. The low molecular weight sugar is used to penetrate and protect intracellular structures during dehydration. The low molecular weight, permeating sugars may be selected from a variety of ketoses, which are non-reducing at neutral or higher pH, or methylated or ethylated monosaccharides. Among the non-reducing ketoses, are included: the six carbon sugars, fructose, sorbose, and piscose; the five carbon sugars, ribulose and xylulose; the four-carbon sugar, erythulose; and the three-carbon sugar, 1,3 dihydroxydimethylketone. Among the methylated monosaccharides, are the alpha and beta methylated forms of gluco, manno, and galacto pyranoside. Among the methylated five carbon compounds are the alpha and beta forms of arabino and xylo pyranosides. Disaccharides, like sucrose, are known to be effective protectants during desiccation because they replace the water of hydration on the surface of biological membranes and macromolecules. In addition, sucrose and/or other fillers may be effectively transformed, by drying under vacuum, into stable foams, composed of thin amorphous films of the concentrated sugar.

Combining monosaccharides with disaccharides and oligosaccharides effectively prevents crystallization of the oligosaccharides during dehydration. In addition, a polymer may be employed to increase the glass transition temperature ($T_g$) of the dehydrated mixture, which may be decreased by inclusion of the low molecular weight monosaccharides. Any biological polymers that are soluble in concentrated sugar solutions may be employed. For example, polysaccharides, like FICOLL, and Dextran, and synthetic polymers, like hydroxyethyl starch, polyethylene glycol, polyvinyl pyrrolidone, polyacrylamide, as well as highly soluble natural and synthetic biopolymers (e.g. proteins) will help to stabilize biological membranes and increase $T_g$.

The ability of some sugars, sugar alcohols, and amino acids such as monosodium glutamate (MSG) to protect biologicals from damage during drying and subsequent storage is known. There are several publications demonstrating the strong protective effect of disaccharides such as sucrose or trehalose for biomacromolecules and membranes. Some investigators use more complex mixtures including monosaccharides (i.e. glucose, fructose etc.) or low molecular weight sugar alcohols (mannitol, sorbitol etc.) to protect cells during freeze-drying. Unlike disaccharides, lower molecular weight sugars and their derivatives better permeate inside cells and provide intracellular protection. For this reason monosaccharides and low molecular weight sugar alcohols have been extensively used in protectant formulations to protect cells and viruses from dehydration damage.

Preservation solutions containing reducing monosaccharides damage sensitive enzymes during storage after drying and that the damage rate quickly increases with increasing storage temperature (see Example 1, below). For this reason, it was hypothesized that reducing monosaccharides could be applied only in cases when freeze-dried specimens were to be stored below 4° C. Alternatively, when biological samples are to be stored at room temperature or higher, the protectant formulation may be selected so as to minimize the reducing power of the protectant(s). In a preferred mode of the present invention, reducing groups of saccharides are methylated in order to obtain enhanced protection. The reducing groups of monosaccharides can also be clorinated, ethylated, etc., in accordance with the present invention.

Low molecular weight carbohydrate additives decrease the glass transition temperature ($T_g$) of suspensions of cells or viruses in the protectant formulation. For example, the $T_g$ of anhydrous fructose is close to 7° C.; the $T_g$ of a 1:1 fructose:sucrose mixture in the anhydrous state is somewhat below 40° C. Glucose has a much higher $T_g$. For this reason, the use of glucose derivatives may be more effective. For example, the $T_g$ of methylated glucose is 29° C. (see FIG. 4).

The plasticizing effect of low molecular weight additives in preservation solutions may be partially offset by the use of soluble higher molecular weight additives that increase $T_g$ in the anhydrous state. In accordance with one preferred embodiment of the present invention, the protectant formuation comprises MSG, a non-reducing oligosaccharide and a soluble protein. In the scope of this patent application we will define the temperatures of between about −20° C. and +50° C. as ambient temperatures, in order to broadly cover most practical applications. However, it is preferred that the methods and formulations disclosed in this application are directed at the preservation of biomolecules, viruses and cells for storage and/or delivery at room temperature (20–25° C.) or higher.

Surprisingly, protectant formulations comprising methylated monosaccharides were particularly effective in protecting viruses and cells. For example, α-methyl glucose (methyl α-d-glucopyranoside) demonstrated unique protective characteristics when preserving sensitive biologicals by drying. This may be because the methyl group is more hydrophobic that the rest of the molecule. For this reason, the methylated sugar will have some amphiphilic behavior, adsorbing preferentially to hydrophobic regions of proteins, virus envelopes, and other membrane structures. This behavior may explain in part the protective effect of methylated glucose. In addition, it is likely that cells which can be loaded with glucose, can also be loaded with α-methyl glucose, in order to provide intracellular protection. Indeed, α-methyl glucose has been used extensively to study glucose transport through the cell membrane. Methylated monosaccharides have not been used in the prior art to preserve biological samples in the dry state.

Unfortunately, solutions of α-methyl glucose in water crystallize during drying. For this reason, α-methyl glucose should be used together with other fillers (i.e. sucrose, trehalose, maltrin, polyvinylpyrrolidone (PVP), proteins etc.) to minimize α-methyl glucose crystallization and to enhance the stability of the amorphous state during drying and subsequent storage. For example, the probability of crystallization of a sucrose/α-methyl glucose solution during drying is dependent on the sucrose/α-methyl glucose mass/mass ratio as discussed and shown with reference to Example 3. Further, the addition of higher molecular weight additives to protectant formulations containing α-methyl glucose will increase the $T_g$ that can be achieved in the dry state.

Primary Foam-Drying—To facilitate scale-up of the processing operations, preservation by foam formation involves the formation of a mechanically stable porous structure by boiling under a vacuum. The drying step is carried out at temperatures in the range of about −15° to 70° C. In one preferred embodiment, the sample temperature during the primary drying step is less than or equal to about 5° C. Preservation by foam formation is particularly well suited for efficient drying of large sample volumes, before vitrification, and as an aid in preparing a readily milled dried product suitable for commercial use. One advantage to foam-dying is that the process is scalable. Thus, the process may be applied for preservation of any volume of solution or suspension containing a sensitive bioactive material, from fractions of a milliliter (for analytical and optimization procedures) to hundreds of liters (for industrial scale production). Further details of preservation by foam formation are included in U.S. Pat. No. 5,766,520 by Bronshtein.

In a variation of the present invention, dilute biological samples may be concentrated by partially removing water before foam-drying under vacuum. This initial concentration step can be accomplished either before or after introduction of the sample into the processing chamber, depending on the concentration method chosen. Alternatively, some samples may be sufficiently concentrated after addition of the protectant molecules, and therefore not require any initial concentration. In situations where it is desirable to increase the concentration of the samples, methods contemplated for use in initial concentration include freeze-drying, evaporation from liquid or partially frozen state, reverse osmosis, other membrane technologies, or any other concentration methods known in the art.

The samples are subjected to vacuum, to cause them to boil during drying at temperatures substantially lower than 100° C. When reduced pressure is applied to solutions or suspensions containing biologically active materials, the solutions or suspensions foam during boiling, and during the foaming process further solvent removal causes the ultimate production of a mechanically-stable open-cell or closed-ell porous foam. The mechanically stable porous structure, or foam, consists of thin amorphous films of the concentrated fillers.

While low vacuum pressures (in the range of 0.1–0.9 atm) may be applied to facilitate the initial evaporation to produce a concentrated, viscous solution, much higher vacuum pressures (0–24 Torr) are used to cause boiling. The vacuum for the boiling step is preferably 0–10 Torr, and most preferably less than about 4 Torr. Boiling in this context means nucleation and growth of bubbles containing water vapor, not air or other gases. In fact in some solutions, it may be advantageous to purge dissolved gases by application of low vacuum (about 0.1–0.9 atm) at room temperature. Such "degassing" may help to prevent the solution from erupting out of the drying vessel. Once the solution is sufficiently concentrated and viscous, high vacuum can be applied to cause controlled boiling or foaming. Concentration of the protectant molecules recited above, in the range of 5–70% by weight, during initial evaporation aids in preventing freezing under subsequent high vacuum and adds to the viscosity, thereby facilitating foaming while limiting uncontrolled eruptions.

Rapid increases in pressure or temperature could cause a foam to collapse. In this case, to enhance the mechanical stability of the porous structures, surfactants may be added as long as those additives do not interfere with the biological activity of the solute intended for conversion to dry form. Moreover, drying of the protectant polymers also contributes to the mechanical stability of the porous structures. Foams prepared according to the present invention may be stored in the processing chamber under vacuum, dry gas, like $N_2$ atmosphere and/or chemical desiccant, prior to subsequent processing operations, (e.g. stability drying, vitrification or milling).

Stability Drying/Vitrification—The mechanically stable foams formed during primary drying, may undergo secondary or "stability" drying at increased temperatures. Since glass transition temperature ($T_g$) is dependent on the water content of the sample and since $T_g$ increases with increased dehydration, different stability drying protocols may be applied depending on the desired storage temperature, to generate a $T_g$ consistent with vitrification (i.e., the formation of a solid amorphous glass) upon cooling to that storage temperature. However, because dehydration of materials is practically impossible once they have entered the glass state, the key to vitrification according to the present invention, where ambient storage temperatures may be desired, is to conduct the stability drying at a temperature significantly higher than the ambient temperature.

Ultimate storage temperatures are preferably within the range of 0°–70° C. More preferably, common storage temperature selections are greater than or equal to 0°, 4°, 20°, 40°, and 50° C. In some cases, where refrigerated storage may be preferred, stability drying could be carried out at room temperature followed by cooling to the storage temperature or below. In other instances, however, where stability at room temperature is desired, dehydration at a temperature above room temperature should be employed, followed by cooling to room temperature.

For any given specimen to be preserved, the nature and stability characteristics of the specimen will determine the maximum temperature it can withstand during the primary drying step. In the case of enzyme preservation, it was shown that after primary drying at room temperature the stability drying temperature may be increased up to 50° C. without loss of enzymatic activity. Then, the dehydration process can be continued during stability drying at higher temperature. Thus, by continuous or step-wise increases in the dehydration temperature, labile proteins can be placed in a state of thermal stability at temperatures well above their denaturation temperature.

In addition to conducting the stability drying at a temperature above the selected storage temperature, it is critical that this drying is carried out for a period of time sufficient to actually raise $T_g$ above the storage temperature. Based on empirical results obtained with dried 10 μl drops of 15% sucrose+15% raffinose solution, it was demonstrated that more than 12 hours of stability drying at temperatures above 70° C. was required to raise $T_g$ to above 25° C. Primary drying in these experiments was for 12 hours at room temperature (20° C.). The results suggest that extended stability drying times (more than 12 hours at 70° C. and more than 60 hours at 50° C.) may be needed to effect increases in $T_g$ over room temperature. For some biological materials which are not heat labile, primary drying at higher temperatures, would reduce the stability drying time at elevated temperatures needed to increase $T_g$ to above the selected storage temperature.

In one embodiment of the present invention, the foam is cooled from stability drying down to the milling temperature, milled, and then the powder is subjected to further drying either under vacuum or at atmospheric pressure. The subsequent drying temperature may be in the range of about 0° to 100° C. Such drying may be continued until the glass transition temperature is raised above a selected storage temperature within the range of about 0° to 70° C.

To ensure that the $T_g$ is actually greater than the storage temperature, at least two methods are known for estimating $T_g$ by thermal analysis. Differential scanning calorimetry (DSC) is the most commonly used technique. However, the Inventor has found that DSC may be unreliable for measuring $T_g$ in samples that contain polymers. Alternatively, Thermally Stimulated Polarization (TSP) methods are specifically adapted for analysis of polymers. The TSP method is preferred because it is reliable for all samples, although it requires slightly larger sample volumes.

The following Examples illustrate various specific aspects of the present invention, relating to preservation mixtures comprising viruses or cells and protectants, wherein the mixtures are adapted to stabilize these samples during dehydration and subsequent storage at ambient and higher temperatures.

EXAMPLE 1

The effect of reducing and non-reducing sugars and PVP on Isocitrate Dehydrogenase (ICDH) was studied during storage at room temperature and 37° C. This experiment is designed to test the reducing capability of additives such as sugars. This reducing property is characterized by the capability to produce the Maillard reaction or enzymatic browning reaction. For monosaccharides or simple sugars, the glycosylic hydroxyl group or OH on the αC is susceptible to chemically react with amino residues containing NH or $NH_2$, e.g. lysine, asparagine.

The enzyme ICDH was formulated in 50% glycerol. The following preservation solutions were used: (1) 30% sucrose+10% PVP solution, (2) 20% glucose+20% PVP solution, (3) 20% fructose+20% PVP solution, and (4) 20% methyl α-d-glucopyranoside+10% PVP solution.

ICDH (200 μl) was dialyzed in cold 0.1 M Tris HCl for 5 hours at 15–17° C. The buffer was stirred gently so that the small molecules were evenly dispersed throughout the solution. After dialysis, the ICDH (total volume=180 μl) was transferred into a 1.7 ml microcentrifuge tube, to which was added 250 μl of 0.1M Tris HCl buffer, pH 7.8. The tube was placed on ice.

The ICDH (100 μl aliquots) was preserved in 1.7 ml microfuge tubes after addition of one of the four different preservation solutions. The preservation mixtures were vortexed and then aliquoted into 40 tubes with 10 μl each. One sample from each of the four different preservation mixtures was assayed at time zero. The remaining samples were dried at room temperature under vacuum overnight. After drying, another sample of each preservation mixture was assayed. The remaining samples were divided into two sets, one for room temperature storage and the other for storage at 37° C. Every two weeks one sample from each preservation mixture and from each storage temperature was assayed for activity.

Figure 1B:
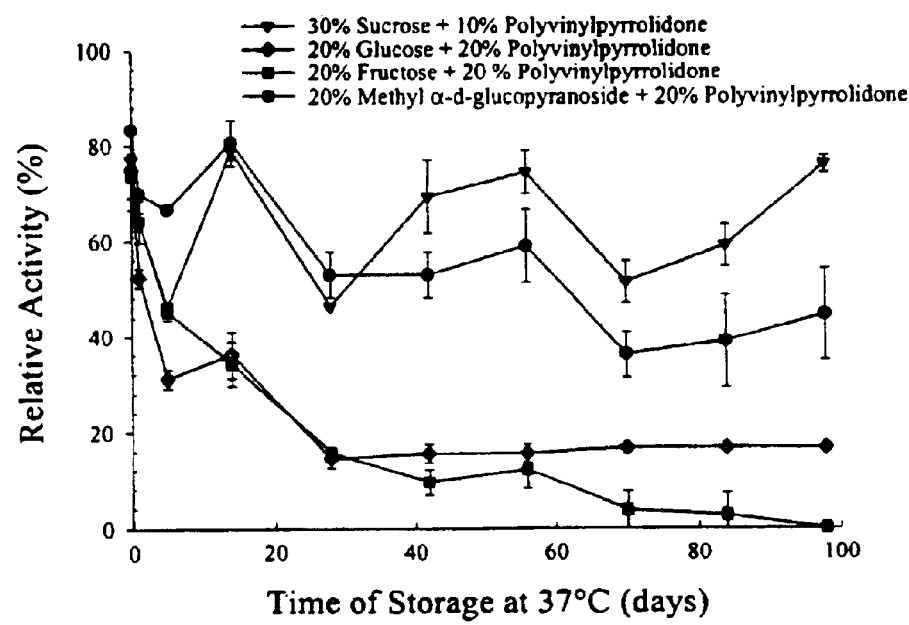
FIG. 1B shows the effect of reducing and non-reducing sugars on ICDH activity during storage at 37° C.

All samples to be assayed, were diluted 10× with 0.1 M Tris HCl, pH 7.8, and mixed by vortexing. The diluted samples (10 μl) were incubated with 3 ml of 0.1 M Tris HCl, pH 7.8, 10 μl of 10 mM $MnSO_4$, 10 μl of 50 mM Isocitrate, and 10 μl of 10 mM $NADP^+$ solution. The absorbance was measured over time at 340 nm. Relative activity was estimated from the changes in absorbance at 20 mV with a chart speed of 4 cm/min. The results are shown in FIGS. 1A and 1B.

EXAMPLE 2

The effect of reducing and non-reducing sugars and PVP on Isocitrate Dehydrogenase (ICDH) was studied during storage at 50° C. This experiment is designed to test the reducing capability of additives such as sugars. This reducing property is characterized by the capability to produce the Maillard reaction or enzymatic browning reaction. For monosaccharides or simple sugars, the glycosylic hydroxyl group or OH on the αC is susceptible to chemically react with amino residues containing NH or $NH_2$, e.g. lysine, asparagine.

The enzyme ICDH was formulated in 50% glycerol. The following preservation solutions were used: (1) 30% sucrose+10% PVP solution, (2) 20% glucose+20% PVP solution, (3) 20% fructose+20% PVP solution, and (4) 20% methyl α-d-glucopyranoside+10% PVP solution.

ICDH (200 μl) was dialyzed in cold 0.1 M Tris HCl for 5 hours at 15–17° C. The buffer was stirred gently so that the small molecules were evenly dispersed throughout the solution. After dialysis, the ICDH (total volume=180 μl) was transferred into a 1.7 ml microcentrifuge tube, to which was added 250 μl of 0.1M Tris HCl buffer, pH 7.8. The tube was placed on ice.

The ICDH (100 μl aliquots) was preserved in 1.7 ml microfuge tubes after addition of one of the four different preservation solutions. The preservation mixtures were vortexed and then aliquoted into 10 μl each. One sample from each of the four different preservation mixtures was assayed at time zero. The remaining samples were dried at room temperature under vacuum overnight. After drying, another sample of each preservation mixture was assayed. The remaining samples stored at 50° C. Every two weeks one sample from each preservation mixture was assayed for activity.

Figure 2:
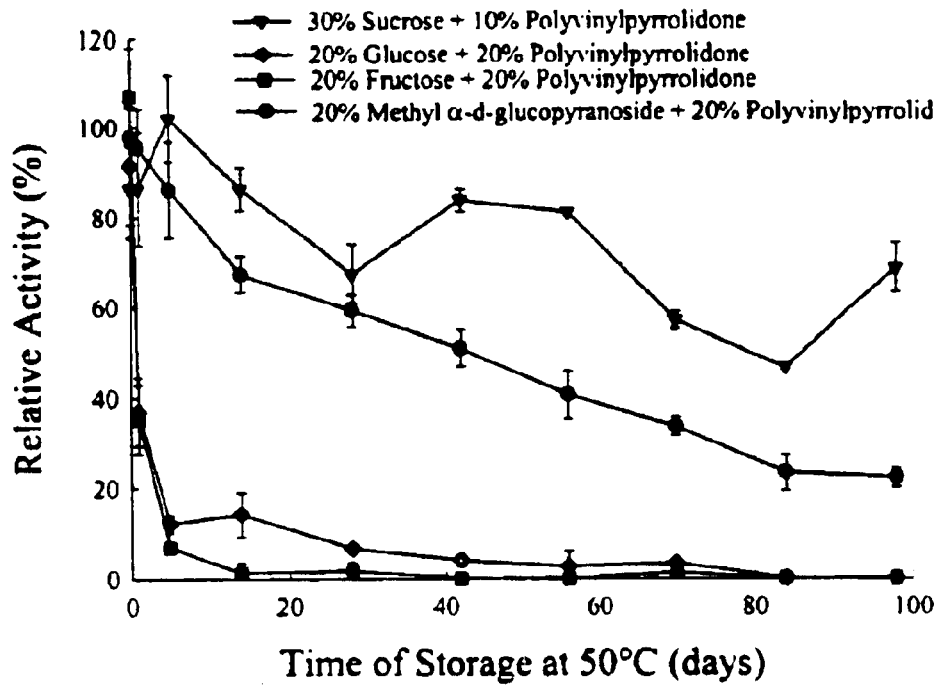
FIG. 2 shows the effect of reducing and non-reducing sugars on ICDH activity during storage at 50° C.

All samples to be assayed, were diluted 10× with 0.1 M Tris HCl, pH 7.8, and mixed by vortexing. The diluted samples (10 μl) were incubated with 3 ml of 0.1 M Tris HCl, pH 7.8, 10 μl of 10 mM $MnSO_4$, 10 μl of 50 mM Isocitrate, and 10 μl of 10 mM $NADP^+$ solution. The absorbance was measured over time at 340 nm. Relative activity was estimated from the changes in absorbance at 20 mV with a chart speed of 4 cm/min. The results are shown in FIG. 2.

EXAMPLE 3

The effect of reducing and non-reducing sugars and maltrin on Isocitrate Dehydrogenase (ICDH) was studied during storage at 50° C. This experiment is designed to test the reducing capability of additives such as sugars. This reducing property is characterized by the capability to produce the Maillard reaction or enzymatic browning reaction. For monosaccharides or simple sugars, the glycosylic hydroxyl group or OH on the αC is susceptible to chemically react with amino residues containing NH or $NH_2$, e.g. lysine, asparagine.

The enzyme ICDH was formulated in 50% glycerol. The following preservation solutions were used: (1) 30% sucrose+10% maltrin solution, (2) 20% glucose+20% maltrin solution, (3) 20% fructose+20% maltrin solution, and (4) 20% methyl α-d-glucopyranoside+10% maltrin solution.

ICDH (200 μl) was dialyzed in cold 0.1 M Tris HCl for 5 hours at 15–17° C. The buffer was stirred gently so that the small molecules were evenly dispersed throughout the solution. After dialysis, the ICDH (total volume=180 μl) was transferred into a 1.7 ml microcentrifuge tube, to which was added 250 μl of 0.1M Tris HCl buffer, pH 7.8. The tube was placed on ice.

The ICDH (100 µl aliquots) was preserved in 1.7 ml microfuge tubes after addition of one of the four different preservation solutions. The preservation mixtures were vortexed and then aliquoted into 10 µl each. One sample from each of the four different preservation mixtures was assayed at time zero. The remaining samples were dried at room temperature under vacuum overnight. After drying, another sample of each preservation mixture was assayed. The remaining samples stored at 50° C. Every two weeks one sample from each preservation mixture was assayed for activity.

Figure 3:
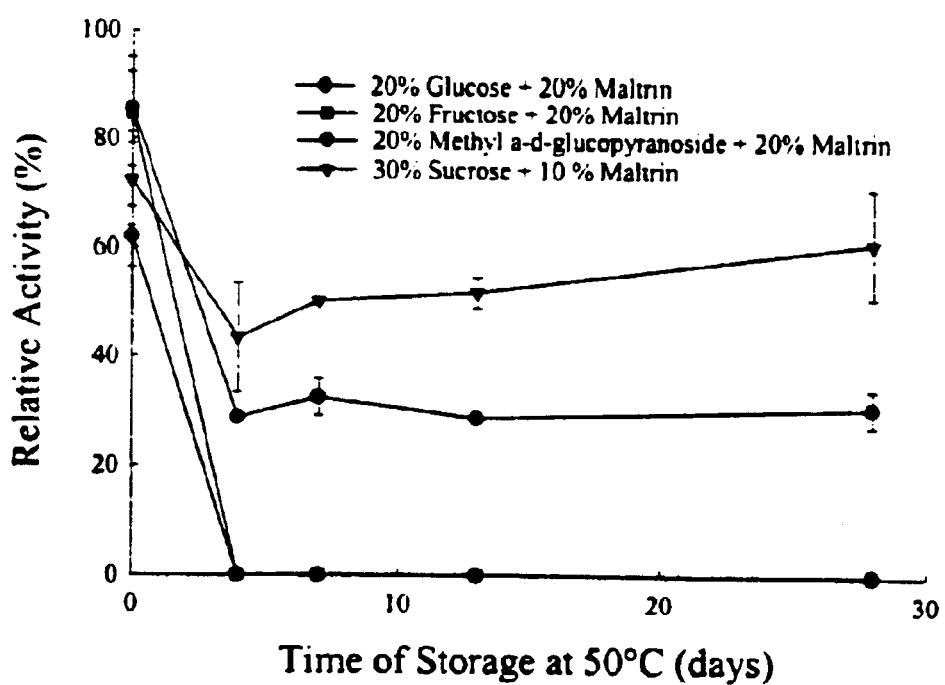
FIG. 3 shows the effect of non-reducing sugars and maltrin on ICDH activity during storage at 50° C.

All samples to be assayed, were diluted 10× with 0.1 M Tris HCl, pH 7.8, and mixed by vortexing. The diluted samples (10 µl) were incubated with 3 ml of 0.1 M Tris HCl, pH 7.8, 10 µl of 10 mM $MnSO_4$, 10 µl of 50 mM Isocitrate, and 10 µl of 10 mM $NADP^+$ solution. The absorbance was measured over time at 340 nm. Relative activity was estimated from the changes in absorbance at 20 mV with a chart speed of 4 cm/min. The results are shown in FIG. 3.

EXAMPLE 4

Figure 4:
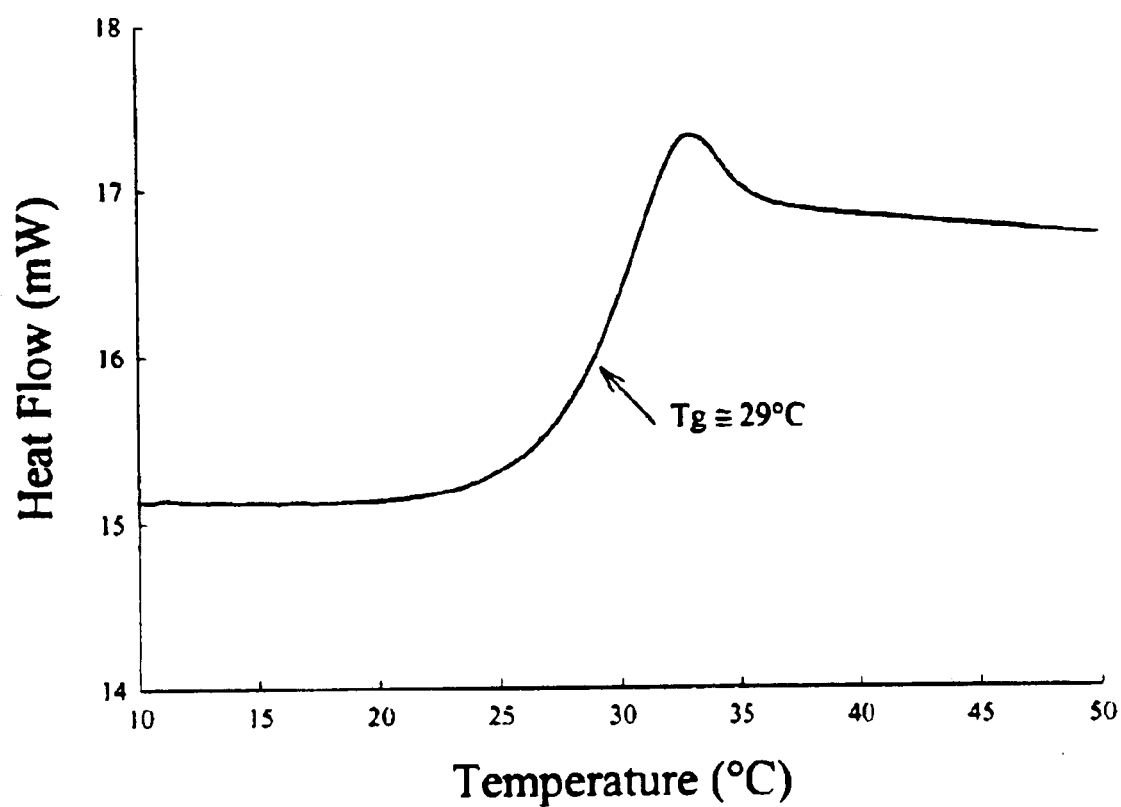
FIG. 4 shows the glass transition temperature of methylated glucose.

To measure the glass transition temperature of methyl α-d-glucopyranoside, the crystals were sealed inside an aluminum pan used for DSC studies. The sample was first melted during heating and then quickly cooled to −100° C. During cooling, the sample vitrified. The glass transition temperature was measured during warming (10° C./min). The change in specific heat associated with glass to liquid transformation, $T_g=29°$ C., is illustrated in FIG. 4.

EXAMPLE 5

The following experiments were carried out in order to be able to assess the capability of formulations to preserve the stability of the amorphous (glass) state during the dehydration process and subsequent storage. Product damage can occur during crystallization or cracking within the glassy matrix. Crystallization is a two step process that occurs in supersaturated or under-cooled solutions. The first step is nucleation with formation of stable nuclei of the phase that will crystallize. The formation of the nuclei is experimentally dependent on the impurities within the material. The stabilization of these nuclei depends on the temperature and concentration of the solutes or co-solutes. The second step is the propagation of the crystallization through the crystal growth processes from the nucleus size. This is also dependent on the temperature and the concentration of the various components within the materials. Nucleation is optimized when the sample is dried close to a complete dehydration state (if the solute crystallization is pure) and crystal growth will be favored if the viscosity is lowered due to the intrinsic kinetics of the growth.

Solutions were prepared in the range of 30 to 50% w/w total solute within the range of solubility of the compounds with different mass ratios between components, as seen in the tables below. All solutions were filtered through 0.02 µm Acrodisc filter units.

The solutions were parsed into droplets on microscope plates and then exposed either to a fast complete drying or to a slow and unfinished dehydration process, as described below. Droplets (10 µl) were placed on alcohol-cleaned microscope slides using a 20 µl pipette to drop ten 10 µl droplets onto each slide, 40 droplets per sample. Prepare boxes with DRIERITE (desiccant) layer. Sample slides were placed into DRIERITE boxes and sealed using parafilm. The number of crystals formed were determined over time and recorded. After two weeks, the samples were transferred into a 52% relative humidity (RH) atmosphere (saturated $Mg(NO_3)_2$). Crystal numbers were again determined over time and recorded. The results are summarized in TABLES 1–6 (below).

TABLE 1

50% Sucrose:MSG Droplet Crystallization

| Ratio Sucrose:MSG | 0% RH storage* | | 52% RH storage** | |
|---|---|---|---|---|
| | week 1 | week 2 | week 1 | week 2 |
| 40:1 | 0.00 | 0.00 | 7.50 | 15.00 |
| 30:1 | 0.00 | 0.00 | 2.50 | 2.50 |
| 20:1 | 0.00 | 0.00 | 0.00 | 0.00 |
| 10:1 | 0.00 | 0.00 | 0.00 | 0.00 |
| 8:1 | 0.00 | 0.00 | 0.00 | 0.00 |
| 6:1 | 0.00 | 0.00 | 0.00 | 0.00 |
| 4:1 | 0.00 | 0.00 | 0.00 | 0.00 |
| 2.5:1 | 0.00 | 0.00 | 0.00 | 0.00 |
| 1:40 | 7.50 | N/A | 12.50 | 15.00 |
| 1:30 | 60.00 | N/A | 77.50 | 77.50 |
| 1:20 | 72.50 | N/A | 75.00 | 75.00 |
| 1:10 | 72.50 | N/A | 75.00 | 75.00 |
| 1:8 | 75.00 | N/A | 80.00 | 80.00 |
| 1:06 | 95.00 | N/A | 95.00 | 95.00 |
| 1:04 | 42.50 | N/A | 42.50 | 42.50 |
| 1:2.5 | 5.00 | N/A | 5.00 | 5.00 |
| 1:01 | 0.00 | N/A | 0.00 | 0.00 |
| 50% MSG | 70.00 | N/A | 70.00 | 70.00 |

*DRIERITE
**$Mg(NO_3)_2$

TABLE 2

50% Sucrose:MSG Droplet Crystallization (Drierite only)

| Ratio Sucrose:MSG | week 1 | week 2 |
|---|---|---|
| 50% sucrose | 0.00 | 0.00 |
| 40:1 | 0.00 | 0.00 |
| 30:1 | 0.00 | 0.00 |
| 20:1 | 0.00 | 0.00 |
| 10:1 | 0.00 | 0.00 |
| 8:1 | 0.00 | 0.00 |
| 6:1 | 0.00 | 0.00 |
| 4:1 | 0.00 | 0.00 |
| 2.5:1 | 0.00 | 0.00 |
| 1:1 | 0.00 | 0.00 |
| 1:2 | 0.00 | 0.00 |
| 1:4 | 2.50 | 2.50 |
| 1:6 | 0.00 | 0.00 |
| 1:8 | 15.00 | 15.00 |
| 1:10 | 65.00 | 65.00 |
| 1:20 | 92.50 | 92.50 |
| 1:30 | 97.50 | 97.50 |
| 1:40 | 2.50 | 2.50 |
| 50% MSG | 100.00 | N/A |

TABLE 3

50% Sucrose:Inositol Droplet Crystallization

| Ratio Inositol:MSG | 0% RH storage* | | 52% RH storage** | |
|---|---|---|---|---|
| | week 1 | week 2 | week 1 | week 2 |
| 4:1 | 90 | 100 | N/A | N/A |
| 6:1 | 100 | N/A | N/A | N/A |
| 8:1 | 0 | 100 | N/A | N/A |
| 10:1 | 0 | 70 | 100 | N/A |
| 12:1 | 0 | 67.5 | 100 | N/A |
| 16:1 | 0 | 0 | 100 | N/A |

TABLE 3-continued

50% Sucrose:Inositol Droplet Crystallization

| Ratio | 0% RH storage* | | 52% RH storage** | |
|---|---|---|---|---|
| Inositol:MSG | week 1 | week 2 | week 1 | week 2 |
| 20:1 | 0 | 0 | 100 | N/A |
| 50% sucrose | 0 | 0 | 12.5 | 22.5 |

DRIERITE
*Mg(NO$_3$)$_2$

TABLE 4

50% Sucrose:Methyl α-d-Glucopyranoside (MAG) Droplet Crystallization

| Ratio Sucrose: | 0% RH storage* | | 52% RH storage** | |
|---|---|---|---|---|
| MAG | week 1 | week 2 | week 1 | week 2 |
| 50% sucrose | 0.00 | 0.00 | 2.50 | NA |
| 40:1 | 0.00 | 2.50 | 2.50 | NA |
| 30:1 | 0.00 | 0.00 | 5.00 | NA |
| 20:1 | 0.00 | 0.00 | 0.00 | NA |
| 10:1 | 0.00 | 0.00 | 2.50 | NA |
| 8:1 | 0.00 | 0.00 | 0.00 | NA |
| 6:1 | 0.00 | 0.00 | 0.00 | NA |
| 4:1 | 0.00 | 0.00 | 0.00 | NA |
| 2:1 | 0.00 | 0.00 | 0.00 | NA |
| 1:1 | 0.00 | 0.00 | 2.50 | NA |
| 1:2 | 0.00 | 0.00 | 7.50 | NA |
| 1:4 | 0.00 | 2.50 | 5.00 | NA |
| 1:6 | 45.00 | 55.00 | 65.00 | NA |
| 1:8 | 22.50 | 47.50 | 67.50 | NA |
| 1:10 | 30.00 | 52.50 | 52.50 | NA |
| 1:20 | 67.50 | 100.00 | N/A | NA |
| 1:30 | 67.50 | 100.00 | N/A | NA |
| 1:40 | 100.00 | N/A | N/A | NA |
| 50% MAG | 100.00 | N/A | N/A | NA |

*DRIERITE
**Mg(NO$_3$)$_2$

TABLE 5

50% MSG:Methyl α-d-Glucopyranoside (MAG) Droplet Crystallization

| Ratio MSG: | 0% RH storage* | | 52% RH storage** |
|---|---|---|---|
| MAG | week 1 | week 2 | week 1 |
| 50% MSG | N/A | N/A | N/A |
| 40:1 | N/A | N/A | N/A |
| 30:1 | N/A | N/A | N/A |
| 20:1 | 45.00 | 45.00 | 45.00 |
| 10:1 | 97.50 | 97.50 | 97.5 |
| 8:1 | 100.00 | N/A | N/A |
| 6:1 | 2.50 | 2.50 | 7.5 |
| 4:1 | 2.50 | 2.50 | 2.5 |
| 2:1 | 0.00 | 0.00 | 0 |
| 1:1 | 0.00 | 0.00 | 35 |
| 1:2 | 2.50 | 7.50 | 17.5 |
| 1:4 | 2.50 | 5.00 | 5 |
| 1:6 | 20.00 | 22.50 | 37.5 |
| 1:8 | 5.00 | 7.50 | 12.5 |
| 1:10 | 87.50 | 87.50 | 95 |
| 1:20 | 37.50 | 45.00 | 55 |
| 1:30 | 87.50 | 90.00 | 95 |
| 1:40 | 70.00 | 92.50 | 92.5 |
| 50% MAG | 100.00 | N/A | N/A |

*DRIERITE
**Mg(NO$_3$)$_2$

When 50% MSG and methyl α-d-glucopyranoside were used, it was noted that at ratios of 40:1 and 30:1, respectively, the solutions had crystallized after they were stored at room temperature overnight (TABLE 5).

With reference to the results shown in TABLE 6 (below), at 50% of 1:10, 1:20, 1:30 and 1:40 ratios of MSG to Trehalose, the solutions crystallized overnight at room temperature. Consequently, no droplets were analyzed for these formulations.

TABLE 6

50% MSG:Trehalose Droplet Crystallization
(Drierite only)

| Ratio MSG:Trehalose | week 1 |
|---|---|
| 50% MSG | 100 |
| 40:1 | 100 |
| 30:1 | 0 |
| 20:1 | 2.5 |
| 10:1 | 0 |
| 8:1 | 5 |
| 6:1 | 0 |
| 4:1 | 0 |
| 2:1 | 0 |
| 1:1 | 0 |
| 1:2 | 0 |
| 1:4 | 100 |
| 1:6 | 0 |
| 1:8 | 100 |
| 1:10 | N/A |
| 1:20 | N/A |
| 1:10 | N/A |
| 1:40 | N/A |
| 50% Trehalose | 100 |

EXAMPLE 6

Bovine Respiratory Syncytial Virus (BRSV), Rhinotracheitis (IBR), Viral Diarrhea (BVD), and Parainfluenza 3 (PI$_3$) viruses were cultured individually and harvested. After harvesting, the viruses were mixed with stabilizer and then dispensed in approximately 40 ml aliquots and then frozen in a −80° C. freezer until processing.

The following 70% w/w preservation solutions were prepared in 0.01 M phosphate buffer and sterile filtered through Corning 0.22 µm PES (Polyesthersulfone) Filter Systems: (1) 2:1 sucrose:methyl α-d-glucopyranoside, (2) 6:1 sucrose:inositol, (3) 2:1 sucrose:isomalt, (4) 5:2 sucrose:sorbitol, (5) trehalose, and (6) 5:2 sucrose:MSG.

All product preparation work was performed in an 18° C. room. Viruses were taken from the −80° C. freezer and placed in cool tap water to thaw (approximately 1 hour). Using aseptic technique, a mixture of the four viruses was prepared in a ratio set in sterile 50 ml polypropylene conical tubes. Two parts of sterile preservation solution was added to one part of viral mixture. A homogenous mixture was obtained by vortexing. For each virus/preservation solution mixture, 2.4 g was loaded into sterile 30 ml borosilicate glass serum vials (Wheaton). A sterile 13 mm finish lyophilization stopper was then placed to the first stop into the mouth of each vial, thereby leaving the notch in the stopper open to allow for water evaporation during preservation by foam formation. Vials were then place on a metal drying tray. The trays were loaded into a pre-cooled (5° C.) freeze-drier modified to execute preservation by foam formation. A thermocouple was placed in one of the vials to monitor the sample temperature during the drying process. The drying process was then performed. After preservation by foam formation was complete, vials were stoppered under vacuum and then removed from the drying machine. Vials were sealed with aluminum crimp seals and held at 4° C. The preserved samples, as well as frozen control samples, were assayed by the following methods.

Madin-Darby Bovine Kidney (MDBK) Cells were maintained in Dulbecco's Modified Eagle Medium (DMEM) with 5% donor horse serum (JRH Biologicals). The serum was antibody and free of BVD, IBR, $PI_3$ and BRSV. The following virus neutralizing sera were obtained from NVSL and used in the virus titration of each fraction of the vaccine: BVDV antiserum NVSL Lot 4X; PI3 antiserum NVSL Lot 86.2; IBRV antiserum NVSL Lot 10×; and BRSV antiserum NVSL Lot 88-5X.

Virus titration for each fraction of the BRSV, IBR, BVD, and $PI_3$ samples was determined by a 4-way vaccine, performed by neutralizing the other three fractions with virus specific antiserum. Cultures of MDBK Cells in a 490 cm$^2$ roller bottle were removed with trypsin-EDTA (Lot #7B2028, JRH Bioscience) and suspended in DMEM+5% horse serum at $1.5 \times 10^5$ cells per ml. The 96-well plates were planted with the cell suspension at 200 µl per well. The microtiter plates were cultured overnight and used the next day for virus titration when the cells were about an 80% confluent monolayer.

Each vial of preserved viruses (4-way vaccine) was rehydrated with 15.5 ml of DMEM. This was considered a $10^{-0}$ dilution. The four vials of each rehydrated vaccine were pooled and used for virus titration. The control viruses were the frozen viruses. A 0.1 ml sample of the rehydrated vaccine was taken and added to a sterile 1 ml vial containing 0.3 ml of each antiserum to the other three viruses. For example, if titrating BVD, 0.1 ml of vaccine was added to a vial containing 0.3 ml anti-IBR serum, 0.3 ml anti-BRSV serum, and 0.3 ml anti-$PI_3$ serum. The total volume at this stage was 1.0 ml and the virus dilution was $10^{-1}$. The mixture was incubated for 40 minutes at room temperature.

Ten-fold dilutions of the viruses were made in 96-well plates by adding 22 µl of the neutralized ($10^{-1}$) samples to the wells (200 µl) on the first row of a plate. Each well was mixed (this was dilution $10^{-2}$) and 22 µl was transferred to the second row, and so forth until finished. Virus titrations were performed in columns 1–10. Columns 11 and 12 were left as uninfected cell controls. The plates were incubated for four days at 37° C. in a 5% $CO_2$ atmosphere. The infection of viruses was determined by cytopathic effect (CPE) readings. Finally, the virus titers were calculated by using the Reed-Muench method. The titers of the four viruses obtained from the control viruses and from the preserved vaccines were recorded, and compared for loss of virus during preservation. The results are shown in TABLE 7; the two numbers reflect the results of duplicate experiments.

TABLE 7

Protective Effects of Methyl α-d-Glucopyranoside and Sugar Alcohols for Preservation of BRSV, IBR, BVD and $PI_3$ Viruses

| Preservation Solution | Initial Survival (%) after Preservation | | | |
|---|---|---|---|---|
| | BRSV | IBR | BVD | $PI_3$ |
| 2:1 sucrose:methyl α-d-glucopyranoside | 57.5, 64.6 | 52.5, 37.2 | 66.1, 58.9 | 125.9, 89.1 |
| 6:1 sucrose:inositol | 38.0, 29.6 | 13.5, 10.7 | 97.7, 24.0 | 67.6, 24.0 |
| 2:1 sucrose:isomalt | 36.3, 33.9 | 16.6, 13.5 | 83.2, 9.8 | 69.2, 26.9 |
| 5:2 sucrose:sorbitol | 35.5 | 17.8 | 2.5 | 28.8 |

TABLE 7-continued

Protective Effects of Methyl α-d-Glucopyranoside and Sugar Alcohols for Preservation of BRSV, IBR, BVD and $PI_3$ Viruses

| Preservation Solution | Initial Survival (%) after Preservation | | | |
|---|---|---|---|---|
| | BRSV | IBR | BVD | $PI_3$ |
| Trehalose | 33.9 | 20.0 | 16.2 | 102.3 |
| 5:2 sucrose:MSG | 21.0, 29.5 | 38.0, 35.5 | 87.1, 49.0 | 91.2, 35.5 |

EXAMPLE 7

Newcastle and Bronchitis viruses were cultured individually and harvested. After harvesting, the viruses were mixed with stabilizer and then dispensed in approximately 200 ml aliquots and frozen at –80° C. Frozen viruses were stored in a –80° C. Revco freezer until processing.

The following 70% w/w preservation solutions in 0.01 M phosphate buffer were prepared and sterile filtered through Corning 0.22 µm PES (Polyesthersulfone) Filter Systems: (1) 2:1 sucrose: methyl α-d-glucopyranoside, (2) 4:1 sucrose:MSG, (3) 4:1 sucrose:maltitol, and (4) 13:1 sucrose:mannitol.

All product preparation work was performed in an 18° C. room. Viruses were taken from the –80° C. freezer and placed in cool tap water to thaw (approximately 2 hours). Using aseptic technique, a mixture of the two viruses was prepared in a 1:1 ratio in sterile 50 ml polypropylene conical tubes. Two parts of preservation solution was added to one part of viral mixture. A homogenous mixture was obtained by vortexing. For each virus/preservation solution mixture, 3.0 g was loaded into sterile 30 ml borosilicate glass serum vials (Wheaton). A sterile 13 mm finish lyophilization stopper was then placed to the first stop into the mouth of each vial, thereby leaving the notch in the stopper open to allow for water evaporation during preservation by foam formation. Vials were then place on a metal drying tray. The trays were loaded into a pre-cooled (5° C.) freeze-drier modified to run the foam preservation method of the present invention. A thermocouple was placed in one of the vials to monitor the sample temperature during the drying process. After preservation, vials were stoppered under vacuum and then removed from the drying machine. Vials were sealed with aluminum crimp seals and held at room temperature or 4° C., depending on the $T_d$ of the drying run (i.e. if $T_d$=30° C., the samples were stored at room temperature; if $T_d$=20° C., the samples were held under refrigeration).

Virus titers were assayed as described above in Example 6. The results of a single experiment are shown in TABLE 8.

TABLE 8

Protective Effects of Methyl α-D-Glucopyranoside and Sugar Alcohols for Preservation of Newcastle and Bronchitis Viruses

| Preservation Solution | Initial Survival (%) after Preservation | |
|---|---|---|
| | Newcastle | Bronchitis |
| 2:1 sucrose:methyl α-d-glucopyranoside | 100 | 20.4 |
| 4:1 sucrose:maltitol | 56.2 | 2.4 |

TABLE 8-continued

Protective Effects of Methyl α-D-Glucopyranoside and Sugar Alcohols for Preservation of Newcastle and Bronchitis Viruses

| Preservation Solution | Initial Survival (%) after Preservation | |
|---|---|---|
| | Newcastle | Bronchitis |
| 13:1 sucrose:mannitol | 55.0 | 4.8 |
| 4:1 sucrose:MSG | 23.4 | 0.4 |

EXAMPLE 8

For preservation of *Streptococcus equi*, the following 70% w/w preservation solutions in 0.01 M phosphate buffer were prepared and sterile filtered through Corning 0.22 μm PES (Polyesthersulfone) Filter Systems: (1) 4:1 sucrose:methyl α-d-glucopyranoside, (2) 1:1 sucrose:methyl α-d-glucopyranoside, and (3) 5:2 sucrose:glutamate.

One vial of frozen seed stock (lot WS012696) was removed from the −80° C. freezer and thawed in cold water. The entire contents (1.0 ml) were transferred to 150 ml of "*S. equi* growth medium" (lot 0757). According to the formula weight, 20 g of 50% Dextrose was added to the medium per liter. The flask was incubated with the cap loosened at 37° C. on the shaker set at 100 rpm for approximately 20 to 24 hours. The culture was allowed to grow until it reached an optical density (OD) of 0.8–1.5, at a wavelength of 600 nm (~12 hours). A purity streak with a loopful of the culture onto TSA II+5% blood agar (lot K1RUWW) was performed. After incubation for 24 to 48 hours at 37° C., the plate was examined and no contamination was detected.

After approximately 23.5 hours of incubation, 10 ml of the pre-culture was transferred into a 500 ml flask with 250 ml of growth medium. The pre-culture was incubated approximately 4 hours under the previously described conditions. Another purity streak onto TSA II+5% blood agar. After incubation for 24 to 48 hours at 37° C., the plate was examined and no contamination was detected. Absorbance of the pre-culture at 600 nm was 1.888.

Approximately 5 hours later, 50 ml from the second pre-culture was inoculated into the fermenter containing 1000 ml of *S. equi* broth+dextrose. The fermentation conditions were: aeration with pressurized oxygen at 1 liter per minute, agitation of 100 rpm, and pH regulation using 2.5 N HCL and 2.5 N NaOH at a temperature of 37° C.

Once the culture reached stationary phase, the cell culture was mixed with preservation solution in a 1:1 weight ratio. A homogenous mixture was obtained by vortexing. For each virus/preservation solution mixture, 1.0 g was loaded into sterile 10 ml borosilicate glass serum vials (Wheaton). A sterile 13 mm finish lyophilization stopper was then placed to the first stop into the mouth of each vial, thereby leaving the notch in the stopper open to allow for water evaporation during the preservation process. Vials were then place on a metal drying tray. The trays were loaded into a pre-cooled (5° C.) freeze-drier modified to execute the foam drying method. A thermocouple was placed in one of the vials to monitor the sample temperature during the drying process. After preservation, vials were stoppered under vacuum and then removed from the drying machine. Vials were sealed with aluminum crimp seals and held at room temperature.

Figure 5:
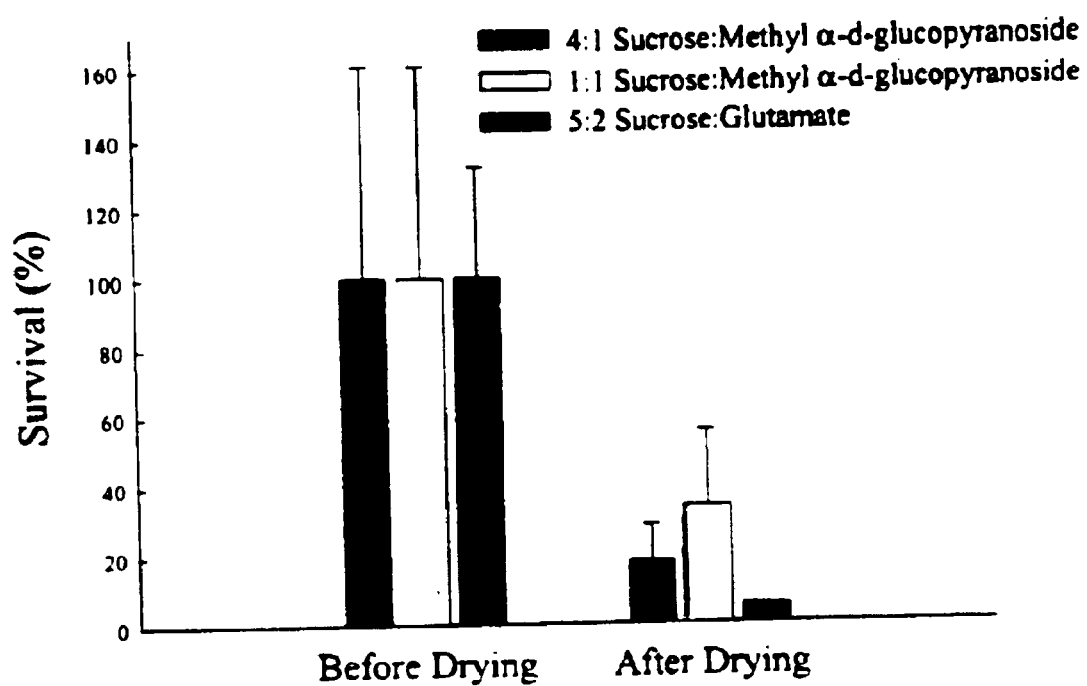
FIG. 5 shows the effect of methyl α-d-glucopyranoside on the preservation of *Streptococcus equi*.

Aliquots (1 g) of each control sample (cell culture+ preservation solution) were diluted 10-fold with PBS. Sample vials from the preserved cells were rehydrated with 10 ml of PBS. The control and preserved samples were further diluted to $10^{-4}$ and $10^{-5}$. Three spread plates of $10^{-5}$ and $10^{-6}$ were prepared on blood agar. The plates were incubated at 37° C. for 48 hours. For all samples, the colonies formed on each plate were counted. The plates that yielded between 30 and 300 colonies were used to calculate the CFU/ml. The CFU/ml for the preserved samples was then divided by CFU/ml from the control samples (cell culture) to determine the % survival after preservation. The results are shown in FIG. 5.

EXAMPLE 9

Bovine Respiratory Syncytial Virus (BRSV), Rhinotracheitis (IBR), Viral Diarrhea (BVD), and Parainfluenza 3 ($PI_3$) viruses were cultured individually and harvested. After harvesting, the viruses were mixed with stabilizer and then dispensed in approximately 40 ml aliquots and then frozen in a −80° C. freezer until processing.

The following 70% w/w preservation solutions were prepared in 0.01 M phosphate buffer and sterile filtered through Corning 0.22 μm PES (Polyesthersulfone) Filter Systems: (1) 2:1 sucrose:methyl α-d-glucopyranoside, (2) 4:1 sucrose:methyl α-d-glucopyranoside, and (3) 5:2 sucrose:raffinose.

All product preparation work was performed in an 18° C. room. Viruses were taken from the −80° C. freezer and placed in cool tap water to thaw (approximately 1 hour). Using aseptic technique, a mixture of the four viruses was prepared in a ratio set in sterile 50 ml polypropylene conical tubes. Two parts of sterile preservation solution was added to one part of viral mixture. A homogenous mixture was obtained by vortexing. For each virus/preservation solution mixture, 2.4 g was loaded into sterile 30 ml borosilicate glass serum vials (Wheaton). A sterile 13 mm finish lyophilization stopper was then placed to the first stop into the mouth of each vial, thereby leaving the notch in the stopper open to allow for water evaporation during preservation by foam formation. Vials were then place on a metal drying tray. The trays were loaded into a pre-cooled (5° C.) freeze-drier modified to execute preservation by foam formation. A thermocouple was placed in one of the vials to monitor the sample temperature during the drying process. The drying process was then performed. After preservation by foam formation was complete, vials were stoppered under vacuum and then removed from the drying machine. Vials were sealed with aluminum crimp seals and held at 4° C. The preserved samples, as well as frozen control samples, were assayed by the following methods.

Madin-Darby Bovine Kidney (MDBK) Cells were maintained in Dulbecco's Modified Eagle Medium (DMEM) with 5% donor horse serum (JRH Biologicals). The serum was antibody and free of BVD, IBR, $PI_3$ and BRSV. The following virus neutralizing sera were obtained from NVSL and used in the virus titration of each fraction of the vaccine:

BVDV antiserum NVSL Lot 4X; PI3 antiserum NVSL Lot 86.2; IBRV antiserum NVSL Lot 10X; and BRSV antiserum NVSL Lot 88-5X.

Virus titration for each fraction of the BRSV, IBR, BVD, and PI$_3$ samples was determined by a 4-way vaccine, performed by neutralizing the other three fractions with virus specific antiserum. Cultures of MDBK Cells in a 490 cm$^2$ roller bottle were removed with trypsin-EDTA (Lot #7B2028, JRH Bioscience) and suspended in DMEM+5% horse serum at 1.5×10$^5$ cells per ml. The 96-well plates were planted with the cell suspension at 200 µl per well. The microtiter plates were cultured overnight and used the next day for virus titration when the cells were about an 80% confluent monolayer.

Each vial of preserved viruses (4-way vaccine) was rehydrated with 15.5 ml of DMEM. This was considered a 10$^{-0}$ dilution. The four vials of each rehydrated vaccine were pooled and used for virus titration. The control viruses were the frozen viruses. A 0.1 ml sample of the rehydrated vaccine was taken and added to a sterile 1 ml vial containing 0.3 ml of each antiserum to the other three viruses. For example, if titrating BVD, 0.1 ml of vaccine was added to a vial containing 0.3 ml anti-IBR serum, 0.3 ml anti-BRSV serum, and 0.3 ml anti-PI$_3$ serum. The total volume at this stage was 1.0 ml and the virus dilution was 10$^{-3}$. The mixture was incubated for 40 minutes at room temperature.

Ten-fold dilutions of the viruses were made in 96-well plates by adding 22 µl of the neutralized (10$^{-1}$) samples to the wells (200 µl) on the first row of a plate. Each well was mixed (this was dilution 10$^{-2}$) and 22 µl was transferred to the second row, and so forth until finished. Virus titrations were performed in columns 1–10. Columns 11 and 12 were left as uninfected cell controls. The plates were incubated for four days at 37° C. in a 5% CO$_2$ atmosphere. The infection of viruses was determined by cytopathic effect (CPE) readings. Finally, the virus titers were calculated by using the Reed-Muench method. The titers of the four viruses obtained from the control viruses and from the preserved vaccines were recorded, and compared for loss of virus during preservation. The results are shown in TABLE 9.

TABLE 9

| Preservation Solution | Survival (%) after Preservation | | | |
|---|---|---|---|---|
| | BRSV | IBR | BVD | PI$_3$ |
| 2:1 sucrose:MAG | 115.0 | 12.6 | 97.7 | 105.0 |
| 4:1 sucrose:MAG | 63.1 | 7.4 | 37.2 | 85.1 |
| 5:2 sucrose:raffinose | 44.7 | 4.6 | 77.6 | 34.7 |

EXAMPLE 10

A formulation of preserved luciferase (Sigma # L-9560) suspended in perfluorodecalin was prepared and tested for stability. Lyophilized luciferase (1 mg) was dissolved with 1 ml of 0.1 M Tris buffer, pH 7.4, containing 1 mg/ml BSA. The resulting 1 mg/ml luciferase solution was dialyzed in 500 ml of 0.1 M Tris buffer, pH 7.4, containing 1 mg/ml BSA at 4° C. for 3.5 hours. The dialyzed luciferase was transferred into a microcentrifuge tube and the luciferase concentration was determined using the following equation:

$$\text{Luciferase concentration} = \frac{\mu g \text{ of initial luciferase}}{\text{final volume of dialyzed luciferase (ml)}}$$

A preservation mixture was prepared by mixing 500 µl of 1 µg/µl dialyzed luciferase with 99.5 g of a 50% 10:1 sucrose:MSG preservation solution. The preservation mixture was then weighed into nine sterile 100 ml serum vials, 10±0.05 g per vial. The remaining dialyzed luciferase was aliquoted into twenty microcentrifuge tubes, 20 µg each, and stored at −80° C. for further use as standard luciferase. The preservation mixture samples were dried to 20° C. for 4.5 hours, then to 45° C. for 60 hours, then to 60° C. for 8 hours, then to 65° C. for 16.5 hours. Samples were then stoppered under vacuum. The vials were moved to a dry room (ambient r.h. ~14%). The vials were opened and the foams scraped out in to a sterile milling flask. The foams were gently milled. The resulting powder was weighed into sterile vials, 1.07 to 1.11 g/vial. 2 ml of perfluorodecalin (Aldrich # p-990-0) was then added to each vial and the vials were stoppered with the dry ambient air and moved to a 37° C. incubator.

Luciferase assay reagent and PBS containing 1 mg/ml BSA was equilibrated at room temperature (RT) for at least 30 min. 9.42 ml of PBS containing 1 mg/ml BSA was added to a milled sample (1 µg/ml) and mixed. 1 µg/ml of this solution was used to make serial dilutions by a factor of 10 to obtain a final concentration of 1×10$^{-5}$ µg/ml. A reaction mixture was prepared by mixing 100 µl of RT luciferase assay reagent with 20 µl of diluted luciferase. The reaction mixture was placed in the luminometer and the light produced was measured every 10 seconds for 1 min. The relative light unit per second (RLU/s) versus relative enzyme concentration (µg/ml) was plotted.

Figure 6:
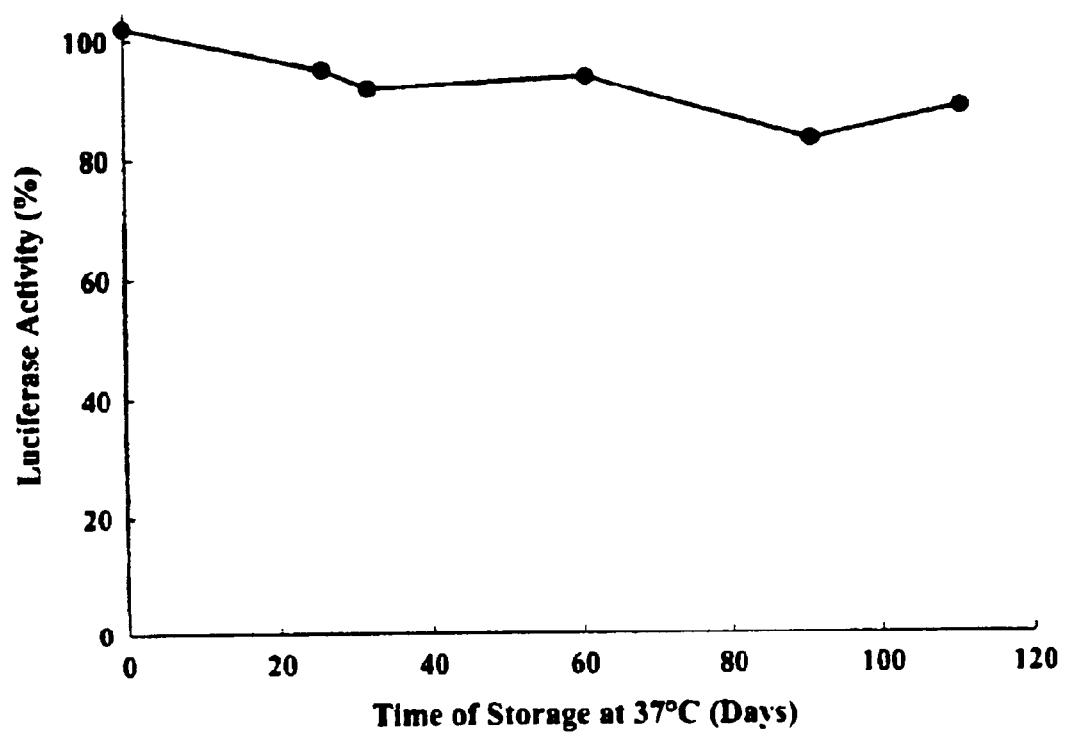
FIG. 6 shows extended stability of dehydrated luciferase in perfluorodecalin during storage at 37° C.

Each time a milled luciferase sample in perfluorodecalin was assayed, a standard luciferase sample was assayed as a control. A standard luciferase assay was performed by first dissolving 1 vial of luciferase assay substrate with 10 ml of luciferase assay buffer and equilibrated at RT for at least 30 min. Then, serial dilutions of standard luciferase were made by a factor of 10 from the original concentration to obtain a concentration in the range of 1×10$^{-5}$ µg/ml to 1 µg/ml. The reaction mixture was prepared by mixing 100 µl of RT luciferase assay reagent with 20 µl of diluted luciferase. The reaction mixture was placed in the luminometer and the light produced was measured every 10 seconds for 1 min. The relative light unit per second (RLU/s) versus relative enzyme concentration (µg/ml) was then plotted. The activity of the milled luciferase in perfluorodecalin was then compared to standard luciferase activity. The results are shown in FIG. 6.

EXAMPLE 11

The bacterial strain *Lactobacillus acidophilus* was grown in a two liter capacity fermenter using a standard protocol specific to the species. The fermenter cell population was counted at 8.1±0.73×10$^8$. The cells were harvested by centrifugation, resulting in 200 ml of cell concentrate with a population of 7.83±0.75×10$^9$. The cell concentrate was diluted in preservation solution consisting of 800 ml of 40% sucrose, 10% methyl α-d-glucopyranoside dissolved in 50% buffer (w/w). The resultant mixture was filled into a polyethylene Petri dish bag at 300 ml. The remainder was reserved for another use. The empty polyethylene bag was attached to a holding device located inside a 4½×19 inch, cylindrical glass chamber supported by an aluminum frame. This glass chamber served as the bulk drying chamber for preservation by foam formation. The test solution was filled into the polyethylene bag with the aid of a length of silicone tubing. The glass chamber was also fitted with an external glass water jacket along the entire tube length. The jacket was coupled to a recirculating, temperature controlled water bath. The water jacket served as the heating source for the process. The glass chamber was connected at the discharge end to the condenser of a lyophilizer. At the conclusion of the preservation by foam formation process, the system vacuum was broken with dry nitrogen. The bag was removed and examined. Dry, mechanically stable, brittle foam had clearly been produced. The material was gently crushed into particles with the consistency of sand, using light hand pressure. The bag was cut open and the contents transferred to a clean container. The container was sampled in triplicate. The container was then purged with dry nitrogen and sealed. The samples were cultured and cell populations compared to control cultures of 1 ml of dried *Lactobacillus acidophilus* foam-dried in 10 ml vials by the same process. Results that demonstrate survival of the test bacterial strain are summarized in TABLE 10.

TABLE 10

| Sample Origin | Plate Count Mean | Plate Count Std. Dev. | Mass Assayed (g) | Volume Diluent (ml) | Activity Cell/g | Average per Sample | % Viable vs. Vial Control |
|---|---|---|---|---|---|---|---|
| Bag A | 1.21E+09 | 0.91E+07 | 0.2415 | 2.4 | 1.21E+09 | 1.12E+09 | 92.50 |
| Bag A | 1.09E+09 | 1.05E+08 | 0.3366 | 3.4 | 1.09E+09 | | 83.10 |
| Bag A | 1.07E+09 | 1.07E+08 | 0.1848 | 1.8 | 1.07E+09 | | 81.32 |

Modification of the above-described modes of carrying out various embodiments of this invention will be apparent to those of skill in the art following the teachings of this invention as set forth herein. The examples described above are not limiting, but are merely exemplary of this invention, the scope of which is defined by the following claims.

What is claimed is:

1. A preservation mixture comprising:
   a virus, bacteria or other cell which is sensitive to loss of viability during drying and storage at ambient or higher temperatures;
   a methylated monosaccharide selected from the group consisting of methyl α-glucopyranoside and methyl β-glucopyanoside; and
   a disaccharide selected from the group consisting of sucrose and trehalose, or alternatively, an oligosaccharide, wherein the preservation mixture has a total solute mass, and wherein the methylated monosaccharide comprises between 5% and 80% wt % of the total solute mass, and the disaccharide, or alternatively an oligosaccharide, comprises between 5% and 80% wt % of the total solute mass.

2. The preservation mixture of claim 1, wherein the methylated monosaccharide comprises between 20% and 60% wt % of the total solute mass.

3. The preservation mixture of claim 1, wherein the disaccharide comprises between 20% and 60% wt % of the total solute mass.

4. The preservation mixture of claim 1, wherein the oligosaccharide comprises between 20% and 60% wt % of the total solute mass.

5. A method of preserving a virus, bacteria or other cell which is sensitive to loss of viability during drying and storage at ambient or higher temperatures, the method comprising:
   mixing the virus, bacteria or other cell with a protectant comprising a methylated monosaccharide selected from the group consisting of methyl (α or β)-glucose and at least one additional compound selected from the group consisting of disaccharides and oligosaccharides to form a preservation mixture, wherein the preservation mixture has a total solute mass, and wherein the methylated monosaccharide comprises between 5% and 80% wt % of the total solute mass, and the disaccharide, or alternatively an oligosaccharide, comprises between 5% and 80% wt % of the total solute mass; and
   drying the preservation mixture by foam formation comprising the formation of a mechanically stable porous foam structure by boiling said preservation mixture under a vacuum.

6. The method of claim 5, wherein said virus, bacteria or other cell further comprises a vaccine or vector.

7. The method of claim 5, wherein the methylated monosaccharide comprises between 20% and 60% wt % of the total solute mass.

8. The method of claim 5, wherein the disaccharide is sucrose or trehalose.

9. The method of claim 5, wherein the disaccharide comprises between 20% and 60% wt % of the total solute mass.

10. The method of claim 5, wherein the oligosaccharide comprises between 20% and 60% wt % of the total solute mass.

11. The method of claim 5, wherein the at least one additional compound is sucrose, and wherein the ratio of sucrose to (α or β)-d-glucose is between 4:1 to 1:2.

12. The method of claim 5, wherein mixing further comprises at least two steps including loading the virus, bacteria or other cell with the methylated monosaccharide and then adding the at least one additional compound to form the preservation mixture.

13. The method of claim 12, wherein loading is achieved by equilibration of the virus, bacteria or other cell in a solution containing the methylated monosaccharide.

14. The method of claim 5, further comprising a step of secondary drying.

15. The method of claim 14, wherein said secondary drying is conducted at a temperature in a range of 0° to 100° C.

16. The method claim 15, wherein said secondary drying is continued until the glass transition temperature is raised above a selected storage temperature within a range of 0° to 70° C.

17. The method of claim 5, further comprising the step of milling said stable foam to form a powder.

18. The method of claim 17, further comprising the step of secondary drying said powder.

* * * * *